United States Patent
Prasad Agara Venkatesha Rao et al.

(10) Patent No.: US 10,856,755 B2
(45) Date of Patent: Dec. 8, 2020

(54) INTELLIGENT PARAMETERIZATION OF TIME-FREQUENCY ANALYSIS OF ENCEPHALOGRAPHY SIGNALS

(71) Applicants: Krishna Prasad Agara Venkatesha Rao, Bengaluru (IN); Srinidhi Srinivasa, Bengaluru (IN)

(72) Inventors: Krishna Prasad Agara Venkatesha Rao, Bengaluru (IN); Srinidhi Srinivasa, Bengaluru (IN)

(73) Assignee: Ricoh Company, Ltd., Tokyo (JP)

( * ) Notice: Subject to any disclaimer, the term of this patent is extended or adjusted under 35 U.S.C. 154(b) by 374 days.

(21) Appl. No.: 15/913,880

(22) Filed: Mar. 6, 2018

(65) Prior Publication Data

US 2019/0274567 A1 Sep. 12, 2019

(51) Int. Cl.
- *A61B 5/04* (2006.01)
- *A61B 5/00* (2006.01)
- *G06F 3/14* (2006.01)

(52) U.S. Cl.
CPC .......... *A61B 5/04012* (2013.01); *A61B 5/726* (2013.01); *A61B 5/7257* (2013.01); *A61B 5/742* (2013.01); *G06F 3/14* (2013.01)

(58) Field of Classification Search
CPC ..... A61B 5/04; A61B 5/04008; A61B 5/7257; A61B 5/726; A61B 5/04012; A61B 5/742; G06F 3/14
See application file for complete search history.

(56) References Cited

U.S. PATENT DOCUMENTS

| | | | | |
|---|---|---|---|---|
| 5,600,373 A | * | 2/1997 | Chui | H04N 19/63 375/240.1 |
| 5,795,304 A | * | 8/1998 | Sun | A61B 5/04884 600/546 |
| 6,697,660 B1 | * | 2/2004 | Robinson | A61B 5/04005 324/248 |
| 6,850,252 B1 | * | 2/2005 | Hoffberg | G06K 9/00369 348/E7.061 |
| 8,533,604 B1 | * | 9/2013 | Parenti | G06F 9/451 715/743 |
| 8,706,214 B2 | * | 4/2014 | Tan | A61B 5/0464 607/5 |
| 9,920,442 B2 | | 3/2018 | Baxter | |
| 9,920,502 B2 | | 3/2018 | Kawasaki et al. | |
| 2002/0128827 A1 | * | 9/2002 | Bu | G10L 15/02 704/222 |
| 2005/0124863 A1 | * | 6/2005 | Cook | A61B 5/04012 600/300 |

(Continued)

*Primary Examiner* — Oommen Jacob
(74) *Attorney, Agent, or Firm* — Fenwick & West LLP (57) ABSTRACT

A system assists users in time and frequency analysis of magnetoencephalography (MEG) signals. In one aspect, a system includes an analysis module, a configuration module and a user interface. The analysis module performs a time and frequency analysis of the MEG signal, for example a short time Fourier transform (STFT) or a continuous wavelet transform (CWT) analysis. The analysis is parameterized by a parameter set that affects the time and frequency resolution of the analysis, for example window size and overlap size for STFT or center frequency and decay parameter for CWT. The configuration module automatically determines or assists the user to determine correct values for the parameter set.

19 Claims, 13 Drawing Sheets
(9 of 13 Drawing Sheet(s) Filed in Color)

(56) References Cited

U.S. PATENT DOCUMENTS

| | | | |
|---|---|---|---|
| 2005/0182456 A1* | 8/2005 | Ziobro | A61B 5/0488 607/48 |
| 2005/0222515 A1* | 10/2005 | Polyshchuk | A61B 7/04 600/528 |
| 2006/0031465 A1* | 2/2006 | Ahya | G06F 9/451 709/224 |
| 2006/0153396 A1* | 7/2006 | John | A61B 5/121 381/60 |
| 2008/0109041 A1* | 5/2008 | de Voir | A61N 1/37 607/7 |
| 2008/0287815 A1* | 11/2008 | Chon | G06F 17/14 600/507 |
| 2009/0067634 A1* | 3/2009 | Oh | H04S 3/008 381/17 |
| 2009/0306531 A1* | 12/2009 | Leuthardt | A61B 5/4836 600/544 |
| 2009/0312919 A1* | 12/2009 | Foster | A01D 41/127 701/50 |
| 2010/0191140 A1* | 7/2010 | Terada | A61B 5/04842 600/544 |
| 2011/0264165 A1* | 10/2011 | Molnar | A61N 1/36185 607/45 |
| 2012/0172017 A1* | 7/2012 | Ratti | H04M 1/72522 455/414.1 |
| 2012/0172743 A1* | 7/2012 | Aguilar | A61B 5/048 600/544 |
| 2013/0109996 A1* | 5/2013 | Turnbull | A61B 5/7264 600/544 |
| 2013/0282379 A1* | 10/2013 | Stephenson | G10L 25/18 704/270 |
| 2013/0303941 A1* | 11/2013 | Porges | A61B 5/126 600/559 |
| 2014/0079248 A1* | 3/2014 | Short | G01S 3/8006 381/119 |
| 2014/0148657 A1* | 5/2014 | Hendler | A61B 5/0476 600/301 |
| 2014/0276181 A1* | 9/2014 | Sun | A61B 5/4094 600/544 |
| 2014/0330394 A1* | 11/2014 | Leuthardt | A61F 2/042 623/25 |
| 2014/0343399 A1* | 11/2014 | Posse | A61B 5/055 600/410 |
| 2015/0196257 A1* | 7/2015 | Yousefi | A61B 5/024 600/324 |
| 2015/0221314 A1* | 8/2015 | Disch | G10L 19/025 704/500 |
| 2016/0157742 A1* | 6/2016 | Huang | A61B 5/04 600/409 |
| 2019/0274567 A1* | 9/2019 | Prasad Agara Venkatesha Rao | A61B 5/04008 |

\* cited by examiner

INTELLIGENT PARAMETERIZATION OF TIME-FREQUENCY ANALYSIS OF ENCEPHALOGRAPHY SIGNALS

BACKGROUND

1. Technical Field

This disclosure relates generally to the analysis of encephalography signals.

2. Description of Related Art

In magnetoencephalography (MEG), the brain's electrical activity causes a magnetic field and this is captured by magnetic field sensors positioned at different locations around the brain. These signals can be analyzed for various purposes, such as diagnosing medical conditions, measuring brain function, and conducting research. They are especially well-suited for detecting temporal responses. In one common scenario, the subject undergoes different types of stimuli or performs different types of activity and the resulting MEG signals are reviewed for certain responses or characteristics. For example, if a known stimulus is presented to the subject, the MEG signals may be observed for a response of a certain frequency at a certain time delay after the stimulus. The presence or absence of that response may be an indication of a medical condition. Statistical analysis can also be performed across populations of subjects, for example between groups with and without a medical conditions.

In many cases, the desired analysis is a time and frequency analysis. That is, the MEG signal is observed in both time and frequency, such as the above example of a response which occurs at a certain frequency after a certain time delay. However, due to the uncertainty principle, there is a tradeoff between time accuracy and frequency accuracy. In order to be very accurate regarding the time when a signal occurs (high time resolution), one must give up frequency resolution. Conversely, in order to be very accurate regarding what frequencies are present in a signal (high frequency resolution), one must give up time resolution.

Thus, an MEG signal may be analyzed with high time resolution and low frequency resolution, high frequency resolution and low time resolution, or some tradeoff between those two. Selecting the correct tradeoff is important to interpreting results and detecting target responses. However, this tradeoff typically is determined by the values of some technical parameters. Selecting different values for these parameters will move the analysis towards higher time resolution or higher frequency resolution. However, in many cases, the user may not understand these parameters or how to set them correctly.

SUMMARY

The present disclosure overcomes the limitations of the prior art by providing a system that assists users in time and frequency analysis of encephalography signals, including magnetoencephalography (MEG) signals. In one aspect, a system includes an analysis module, a configuration module and a user interface. The analysis module performs a time and frequency analysis of the MEG signal, for example a short time Fourier transform (STFT) or a continuous wavelet transform (CWT) analysis. The analysis is parameterized by a parameter set that affects the time and frequency resolution of the analysis, for example window size and overlap size for STFT or center frequency and decay parameter for CWT. The configuration module automatically determines and/or assists the user to determine values for the parameter set.

Other aspects include components, devices, systems, improvements, methods, processes, applications, computer readable mediums, and other technologies related to any of the above, including application to other types of encephalography signals.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the disclosure have other advantages and features which will be more readily apparent from the following detailed description and the appended claims, when taken in conjunction with the examples in the accompanying drawings, in which:

DETAILED DESCRIPTION OF THE PREFERRED EMBODIMENTS

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Figure 1:
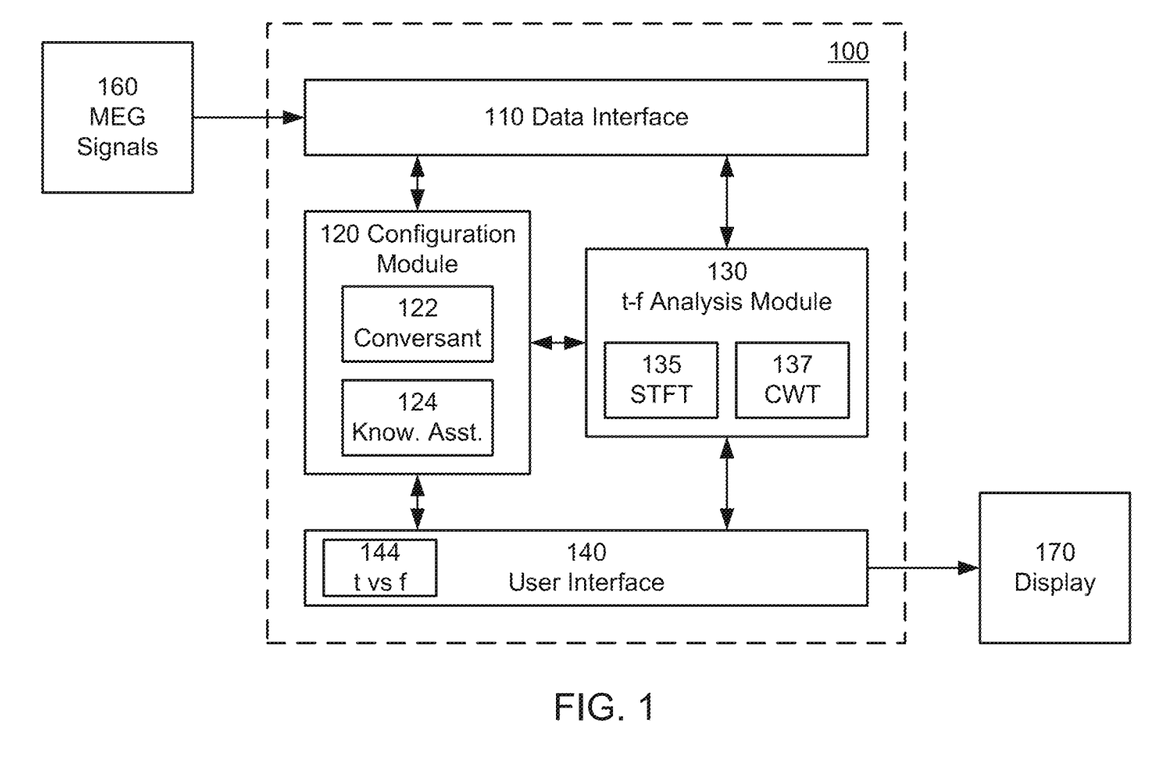
FIG. 1 shows a block diagram of a system for analyzing magnetoencephalography (MEG) signals, according to an embodiment.

FIG. 1 shows a block diagram of a system for analyzing magnetoencephalography (MEG) signals, according to an embodiment. The system 100 accesses MEG signals 160, performs some time and frequency analysis on the signals, and displays 170 the result to the user. In this example, the system 100 includes a data interface 110, a configuration module 120, a time and frequency analysis module 130 and a user interface 140. The data interface 110 provides access to the MEG signals 160. For example, it may access a database containing previously captured MEG signals, with the system 100 analyzing the signals post-capture. Alternately, the data interface 110 may be an interface to MEG hardware that is capturing MEG signals, with the system 100 providing real-time analysis and display of the signals. The user interface 140 displays the time and frequency analysis and also receives user input, as will be described below.

The analysis module 130 performs the time and frequency analysis. Two examples of time and frequency analysis are short time Fourier transform (STFT) 135 and continuous wavelet transform (CWT) 137, although other types of time and frequency analysis such as the Hilbert transform may also be performed. Often, the analysis has a set of parameters that can be adjusted. For example, window size and overlap size are common parameters for STFT analysis, while center frequency and a decay parameter are common parameters for CWT analysis. The parameter set affects the time and frequency resolutions of the analysis.

The configuration module 120 determines the values for the parameter set. In FIG. 1, the configuration module 120 includes a conversant 122 and a knowledge assistant 124. The conversant 122 is a natural language translator. It communicates with the user using natural language to collect semantic requirements. These semantic requirements are of clinical or analytical importance and provide information about appropriate values for the parameter set. They may or may not be sufficient to directly specify the values for the actual parameters. For example, the conversant 122 may receive user inputs such as "detect a range of frequencies with the best possible time lag or temporal resolution" or "detect a range of frequencies with good frequency resolution" or "focus on alpha band." It can also receive user inputs that can be directly used to set parameter values, such as "set window size to 512" or "set overlap size to 50% of window size" or "increase center frequency by 20%."

The knowledge assistant 124 determines values of the parameter set based on the MEG signal being analyzed and/or based on user input, including user input from the conversant 122. The parameter set is used by the analysis module 130 in performing the time and frequency analysis.

Figure 2:
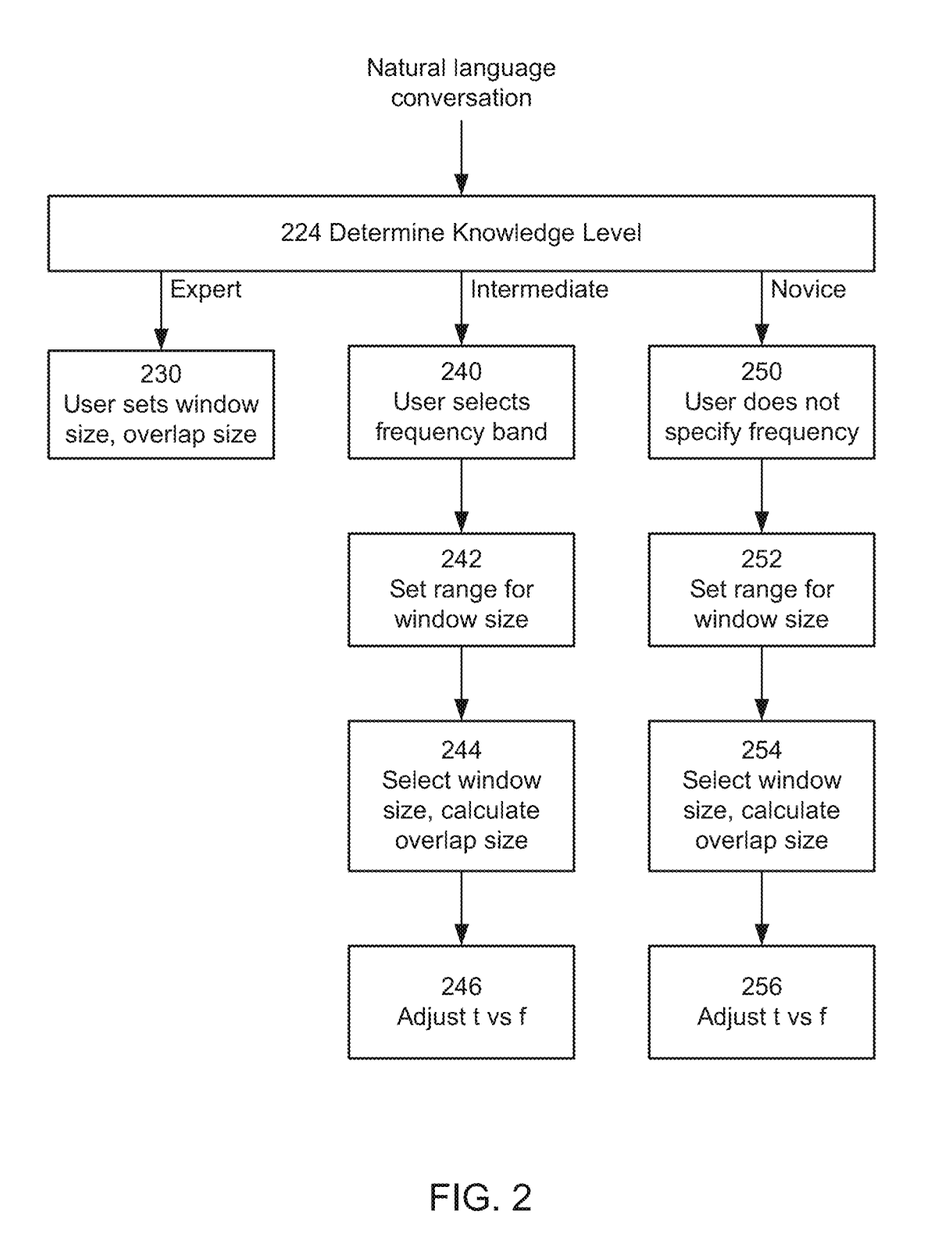
FIG. 2 shows a flow diagram illustrating one mode of operation of the system of FIG. 1 using the short time Fourier transform (STFT).

FIG. 2 shows a flow diagram illustrating one mode of operation of the system of FIG. 1 using the short time Fourier transform (STFT). Here, the time and frequency analysis is a STFT analysis 135, with a parameter set that includes window size and overlap size. Window size is the size of the sample to which the Fourier transform is applied. It may be specified by the number of sample points or by the time period covered by the sample (for a given sampling rate). For a given sampling rate, smaller window sizes are shorter time samples and result in higher time resolution but lower frequency resolution. Conversely, larger window sizes are longer time samples and result in lower time resolution but higher frequency resolution. Overlap size is the amount by which adjacent windows overlap. Overlap reduces the effect of spectral leakage because window functions typically taper towards the window edge. In one approach, the overlap size is set to a percentage of the window size, for example 25% or 50% of the window size. This reduces the parameter set from two degrees of freedom to one.

In FIG. 2, the knowledge assistant 124 determines 224 the knowledge level of the user based on the natural language conversation between the user and the conversant 122. In this example, there are three knowledge levels: Expert, Intermediate and Novice. Expert users directly set values for the parameter set. For Novice users, the configuration module provides more guidance. It may select a range of values and default values for the parameter set based on an analysis of the MEG signal. The user can adjust these not directly, but using a more intuitive approach. For example, the user interface may allow the user to request better frequency resolution or better time resolution, and the configuration module then adjusts the parameter set accordingly. Intermediate users are in between.

The user is Expert 230 if the conversation indicates that the user knows how and what parameters to tune to achieve the desired results, and the Expert user directly sets the window size and overlap size. The conversation may include enough information to directly set the parameters: "set window size to 128", "set overlap size to 32", etc. Alternately, once the user is classified as Expert, the knowledge assistant 124 may direct the conversant 122 to ask questions to obtain this information: "what is the window size?" "should I use overlap size equal to fifty percent of window size?".

Consider next the Novice user. If the conversation indicates that the user has little to no knowledge about appropriate values for the parameter set, of even what parameters are available or typically used, then the user is classified as Novice 250. Typically, the Novice's conversation will contain little to no information that is directly useful to setting the parameters. The knowledge assistant 124 makes the analysis easier for the Novice user by letting the user specify a relative importance between time accuracy and frequency accuracy and automatically computing the parameter set based on this.

Alternately, the knowledge assistant 124 may automatically set the parameters based on available information and without user input. For example, the knowledge assistant 124 may select the parameter set based on a coarse frequency analysis of the MEG signal. One example is shown by process 252-256.

Figure 3A:
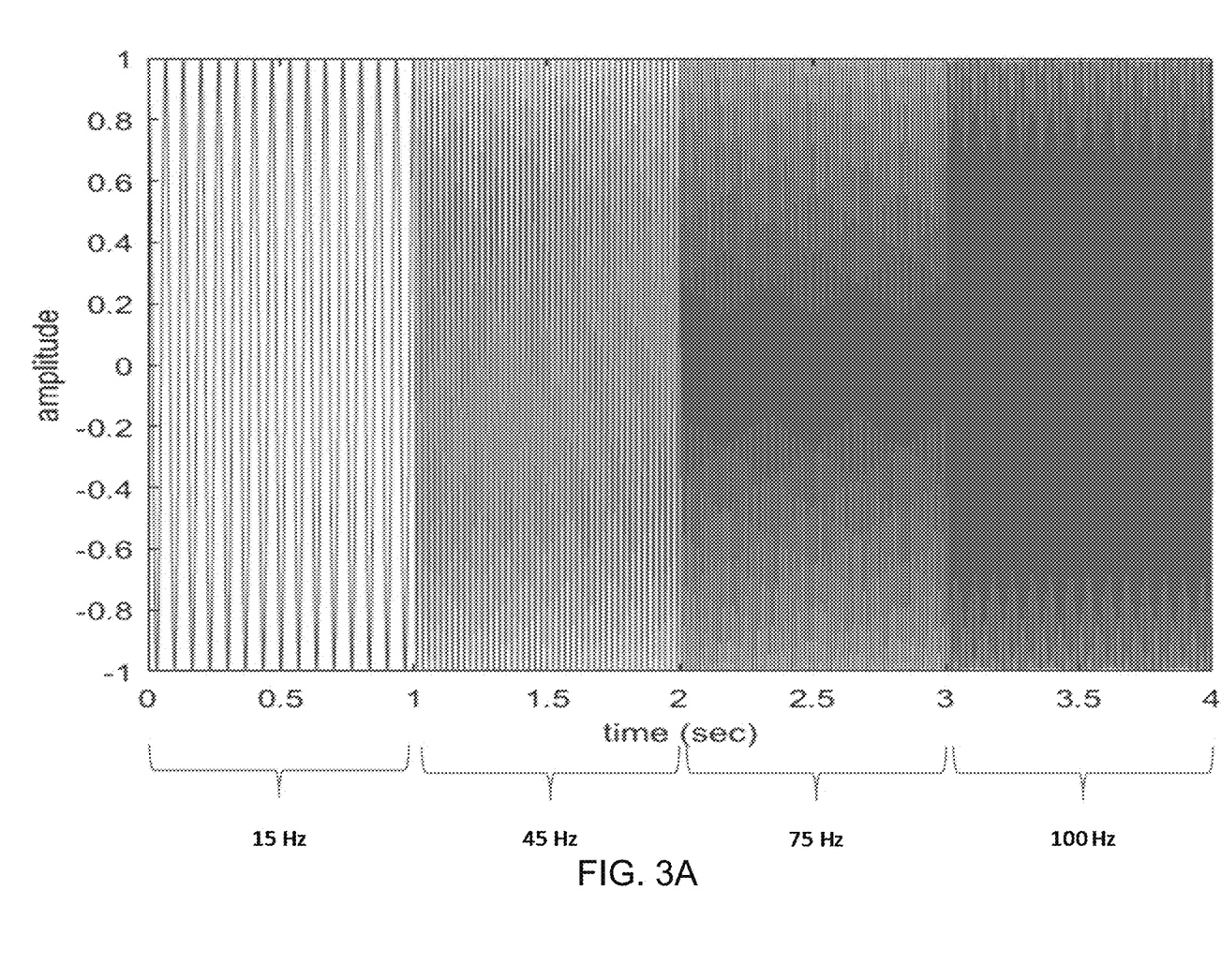
FIG. 3A shows a time plot of a chirp signal.

FIG. 3A shows a time plot of a chirp signal, which will be used to illustrate process 252-256. This chirp signal has four regions: 15 Hz for 0-1 sec, 45 Hz for 1-2 sec, 75 Hz for 2-3 sec and 100 Hz for 3-4 sec. The knowledge assistant 124 determines 252 a range of possible window sizes based on a frequency analysis of the MEG signal. In one implementation, this is a coarse Fourier transform of the entire MEG signal. The M strongest frequencies are identified. Other methods can also be used to identify the strongest frequencies, such as thresholding or percentile cutoffs or frequencies identified based on statistical analysis. For convenience, these strongest frequencies will be referred to as the primary frequencies.

Figure 3B:
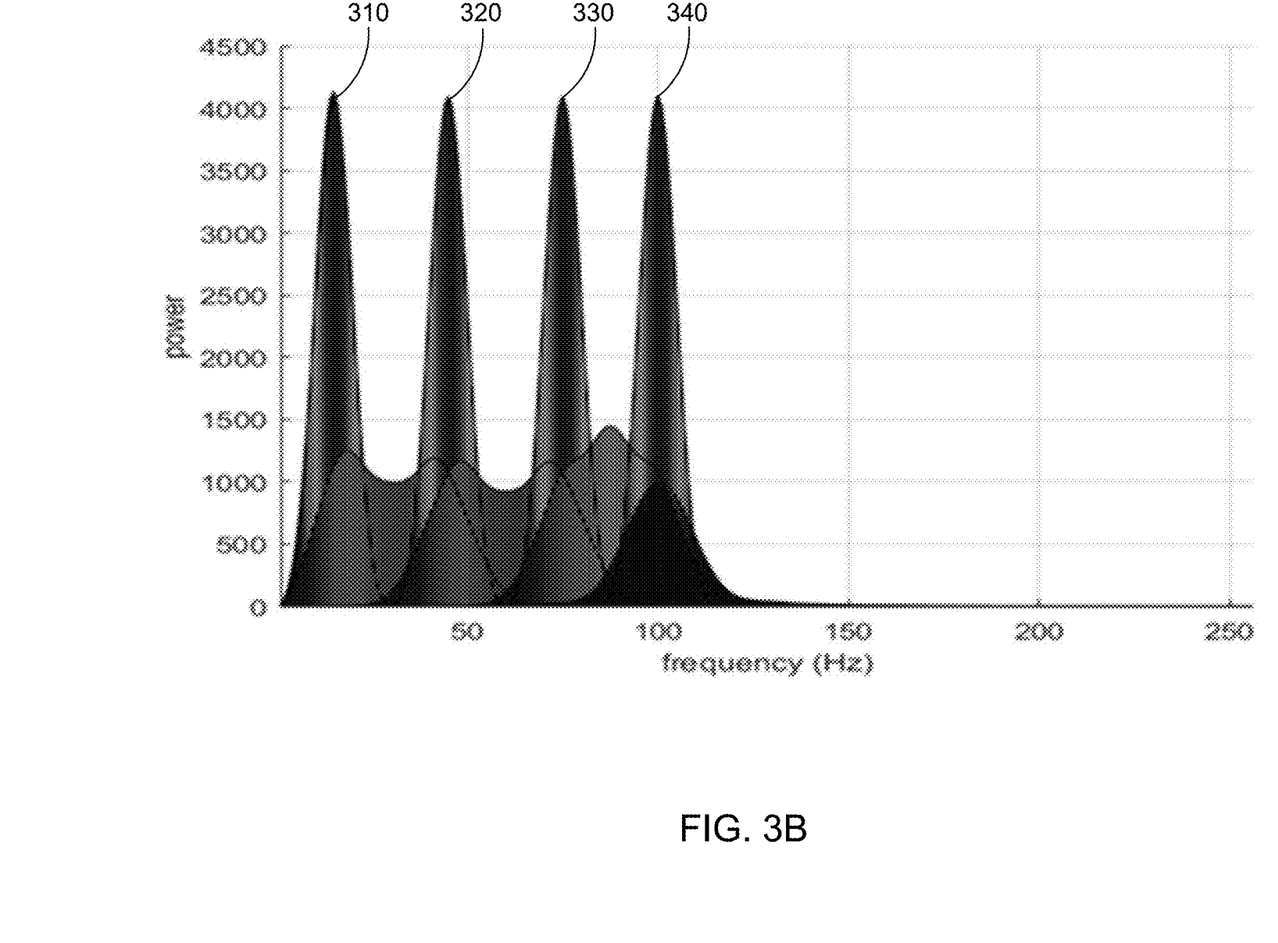
FIG. 3B plots a Fourier transform of the chirp signal of FIG. 3A.

FIG. 3B plots a Fourier transform of the chirp signal of FIG. 3A. This is a coarse Fourier transform. The chirp signal has four primary frequencies 310, 320, 330 and 340, at 15, 45, 75 and 100 Hz.

The knowledge assistant 124 sets 254 the range of possible window sizes as follows:

Min window size=based on 2× the lowest primary frequency=2×15 Hz in this example=30 samples. This would yield the highest time resolution.

Max window size=size of full MEG signal=1000 samples. This would yield the lowest time resolution.

Default window size=based on 2× the highest primary frequency=2×100 Hz=200 samples.

This example uses a multiplier of 2×, but other multipliers could also be used.

The user interface 140 includes an input mechanism 144 to allow the user to vary 256 the tradeoff between time and frequency. For example, the user interface 140 may include a slider or scroll bar 144, with one side representing high time accuracy and the other side representing high frequency accuracy.

Figure 4A:
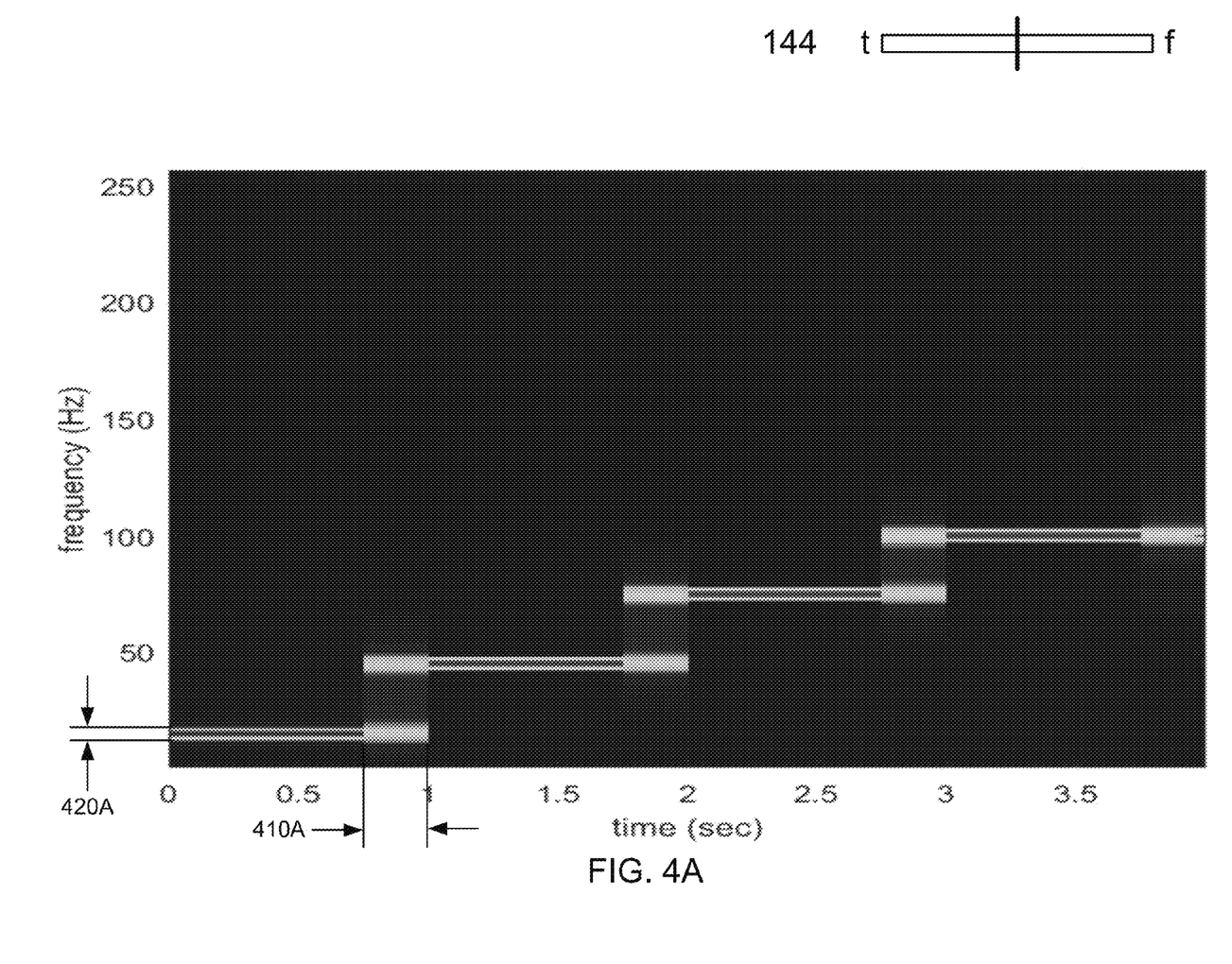
FIGS. 4A-4C show time-frequency plots of STFT analysis of MEG signals with different emphasis on time versus frequency, according to an embodiment.
Figure 4B:
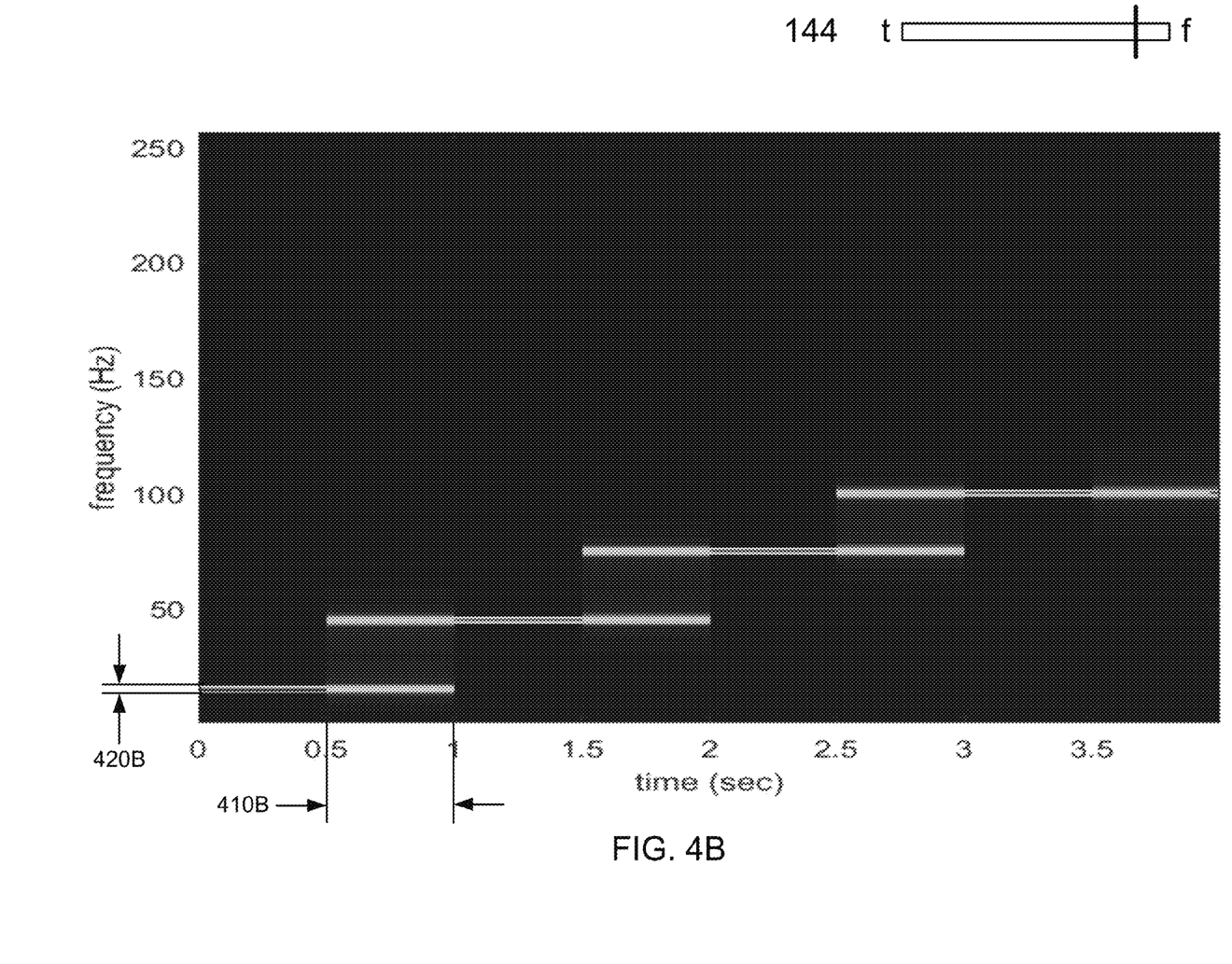
Figure 4C:
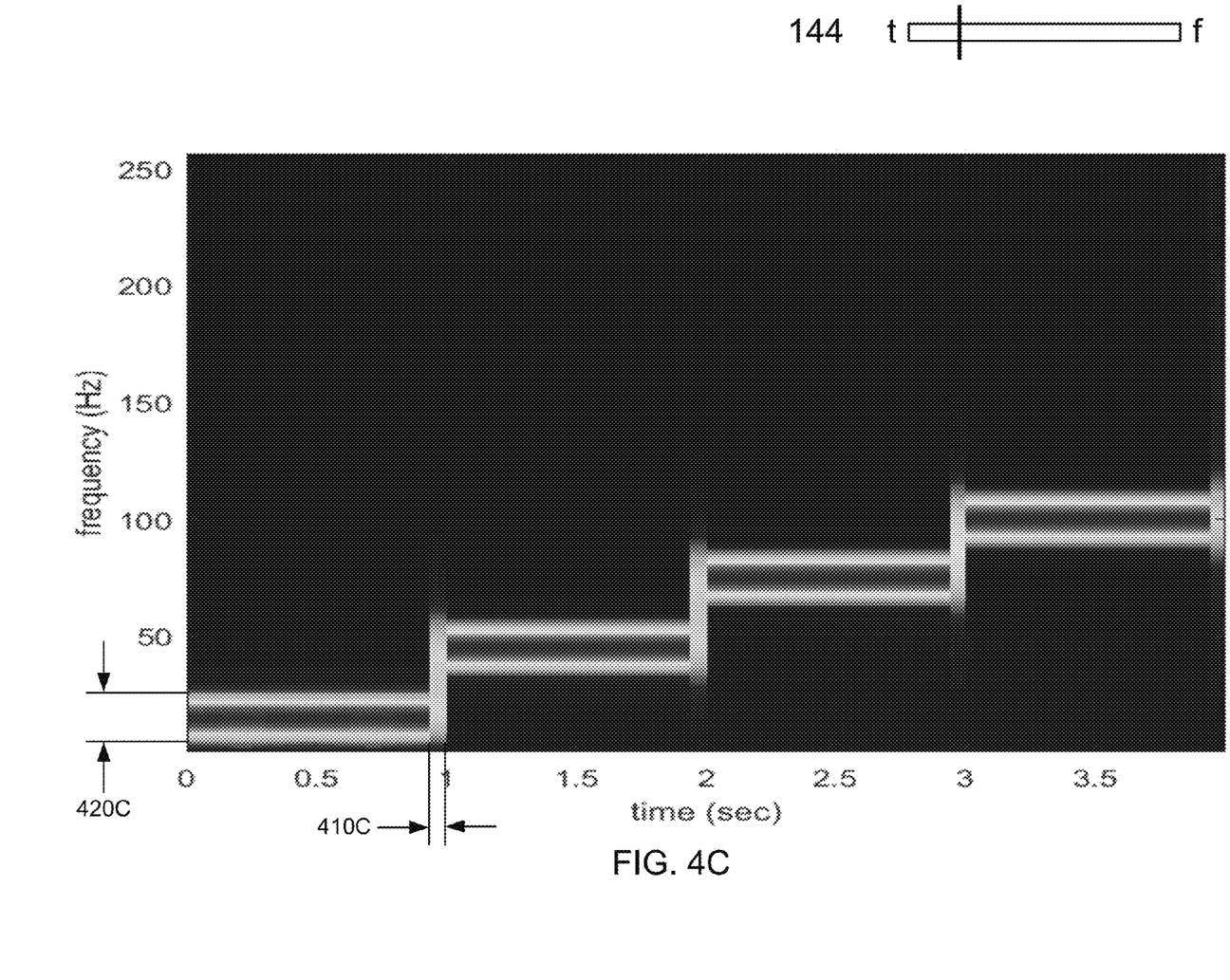

FIGS. 4A-4C show time-frequency plots of STFT analysis of MEG signals with different emphasis on time versus frequency, according to an embodiment. These are time-frequency plots of short time Fourier transform analysis of the chirp signal of FIG. 3A. In these figures, the color indicates the strength of the response, with warmer colors (towards red) indicating higher power and cooler colors (towards blue) indicating lower power. FIG. 4A is a time-frequency plot of the STFT analysis using the default window size=200 samples, with the overlap size set to 50% of the window size. The upper right shows a slider 144 from the user interface, where "t" indicates high time accuracy and "f" indicates high frequency accuracy. In FIG. 4A, the slider is set midway between t and f. The time uncertainty 410A is approximately 0.25 sec and the frequency uncertainty 420A is approximately 5 Hz.

In FIG. 4B, the user has moved the slider 144 towards the "f", indicating a desire for higher frequency accuracy. The knowledge assistant 124 converts this request into a longer window size, in this case window size=400 samples. The knowledge assistant 124 also recalculates the overlap size as 50% of the new window size. In an alternate approach, the overlap size can be reduced as the window size increases, subject to some minimum overlap size. The resulting display in FIG. 4B has a better frequency uncertainty 420B of approximately 2.5 Hz, but with a higher time uncertainty 410B of approximately 0.5 sec.

FIG. 4C shows the reverse situation where the user has moved the slider 144 towards the "t", indicating a desire for higher time accuracy. The knowledge assistant 124 converts this request into a shorter window size, in this case window size=40 samples. The knowledge assistant 124 also recalculates the overlap size. The resulting display in FIG. 4C has a better time uncertainty 410C of approximately 0.05 sec, with a worse frequency uncertainty 420C of approximately 25 Hz.

Returning to FIG. 2, in some cases, the knowledge assistant 124 may determine that the user has intermediate knowledge. The user has provided some information affecting the parameter set, but not enough to determine specific values for the parameter set or to conclude that the user could effectively directly select values for the parameters. In this example, the conversation with the user indicates 240 that a certain frequency band is of interest. Table I lists the major frequency bands common to MEG analysis:

TABLE I

Common frequency bands for MEG analysis

| Frequency Band | Frequency Range |
|---|---|
| Delta | 0.1-4 Hz |
| Theta | 4-8 Hz |
| Alpha | 8-12 Hz |
| Beta | 12-40 Hz |
| Gamma | 40-100 Hz |

In one approach, the frequency band(s) of interest are determined based on natural language processing of the conversation with the user. In another approach, the user expressly selects the frequency band(s), for example from a drop-down menu.

Figure 5:
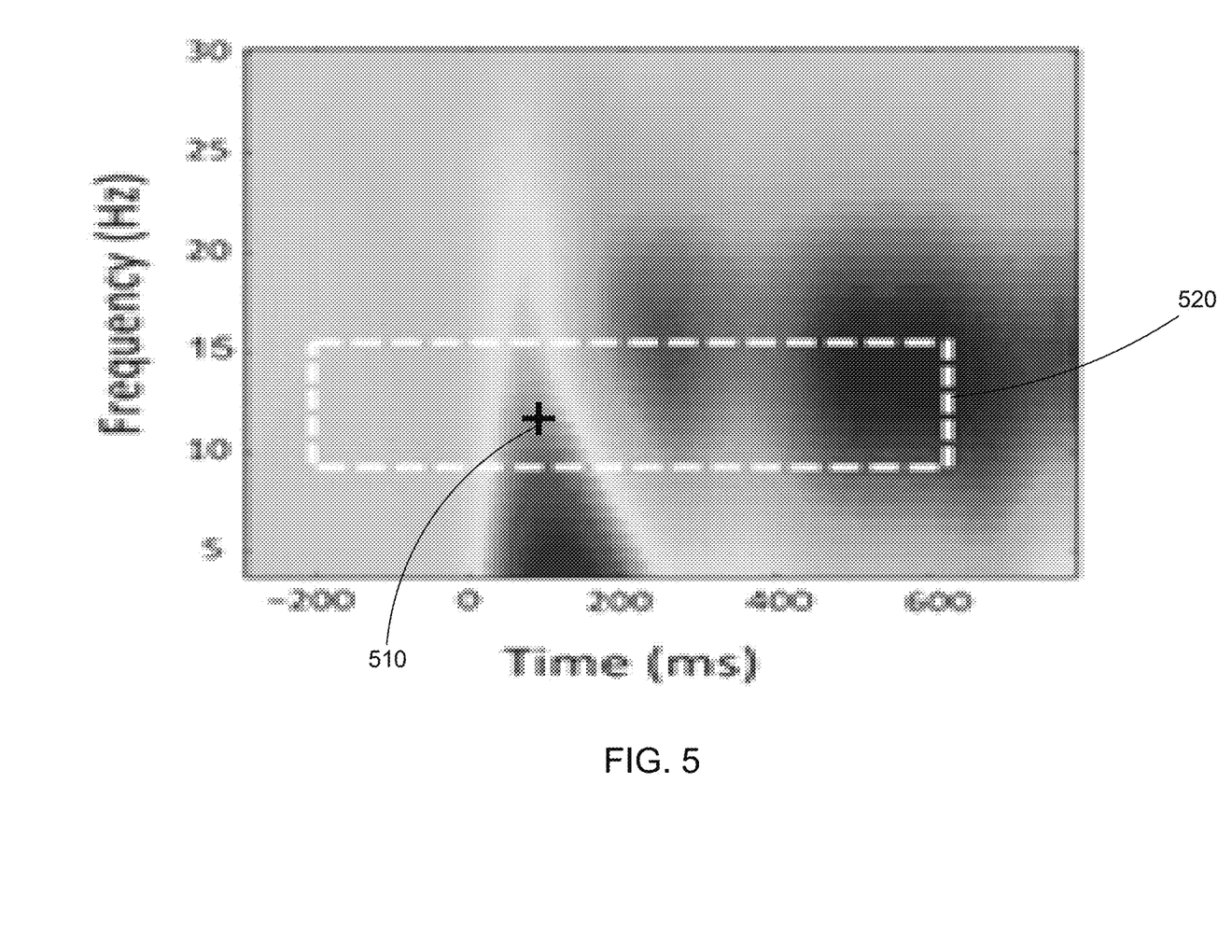
FIG. 5 shows a time-frequency plot of a MEG signal illustrating user selection of a frequency band, according to an embodiment.

Alternatively, the user might graphically indicate the frequency band of interest by selecting areas of interest on a time-frequency plot. This approach is shown in FIG. 5. FIG. 5 shows a time-frequency plot of a MEG signal illustrating user selection of a frequency band, according to an embodiment. Warmer colors indicate higher powers. The user positions his cursor 510 to indicate a point of interest.

In this example, the point of interest is approximately 11 Hz, which is in the alpha band. The knowledge assistant 124 selects the alpha band as the frequency band of interest. It then determines 242 a range of possible window sizes based on this frequency band of 8-12 Hz, as follows:

Min window size=based on 2× the low end of the alpha band=2×8 Hz
  Max window size=based on 2× the high end of the alpha band=2×12 Hz
  Default window size=based on 2× the user-selected frequency=2×11 Hz The knowledge assistant 124 calculates 244 an initial window size and overlap size based on the default window size. The user can adjust 246 the time vs frequency tradeoff graphically on the time-frequency plot or by using a mechanism such as the slider bar 144 in FIGS. 4A-4C.

In an alternate approach, the user might indicate an area of interest, for example by drawing a rectangle 520.

Figure 6:
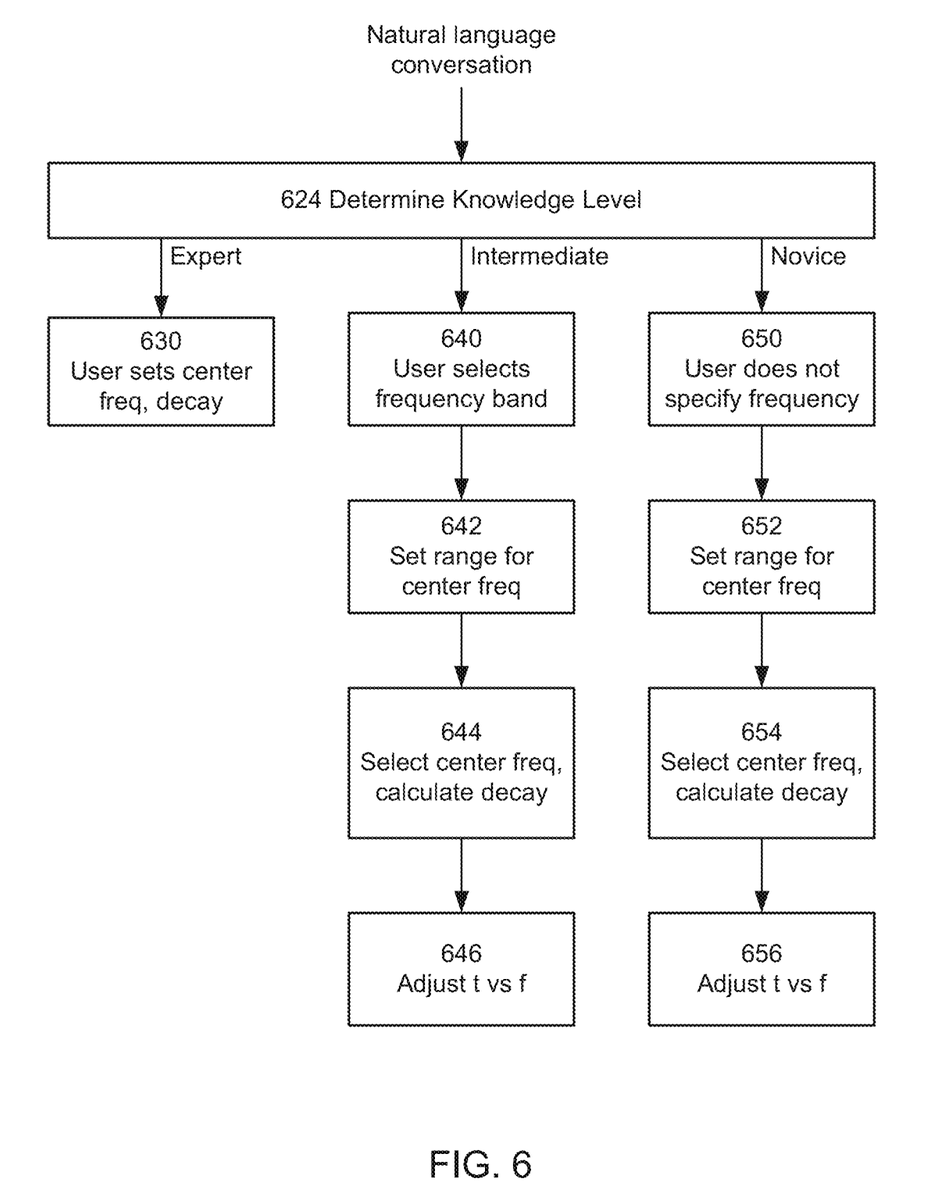
FIG. 6 shows a flow diagram illustrating another mode of operation of the system of FIG. 1 using the continuous wavelet transform (CWT).

FIG. 6 shows a flow diagram illustrating another mode of operation of the system of FIG. 1 using the continuous wavelet transform (CWT). Here, the time and frequency analysis is a CWT analysis 137, with a parameter set of center frequency and decay parameter. Center frequency is the center frequency of the mother wavelet. Higher center frequencies tend to have better frequency accuracy and lower center frequencies tend to have better time accuracy. Decay can be specified by different parameters. Full width half max (FWHM) is a measure of decay in the time domain and the bandwidth parameter (FB) is a measure of decay in the frequency domain. The choice of mother wavelet may be another parameter for CWT analysis.

The process of FIG. 6 for CWT is analogous to the process of FIG. 2 for STFT. The knowledge assistant 124 classifies 624 the user as Expert, Intermediate or Novice. The Expert user directly sets 630 the center frequency and decay parameter. For Novice users 650, a similar approach is taken as in FIG. 2. The knowledge assistant 124 determines 652 a range of possible center frequencies based on a frequency analysis of the MEG signal. For example, the range might be set as follows:

Min center frequency=half the lowest primary frequency
  Max center frequency=half the highest primary frequency
  Default center frequency=average of min and max center frequencies The decay parameter may be calculated 654 as a function of the center frequency. The user can then select within this range by adjusting 656 the time versus frequency tradeoff, thus avoiding having to directly select values for the parameter set.

Figure 7A:
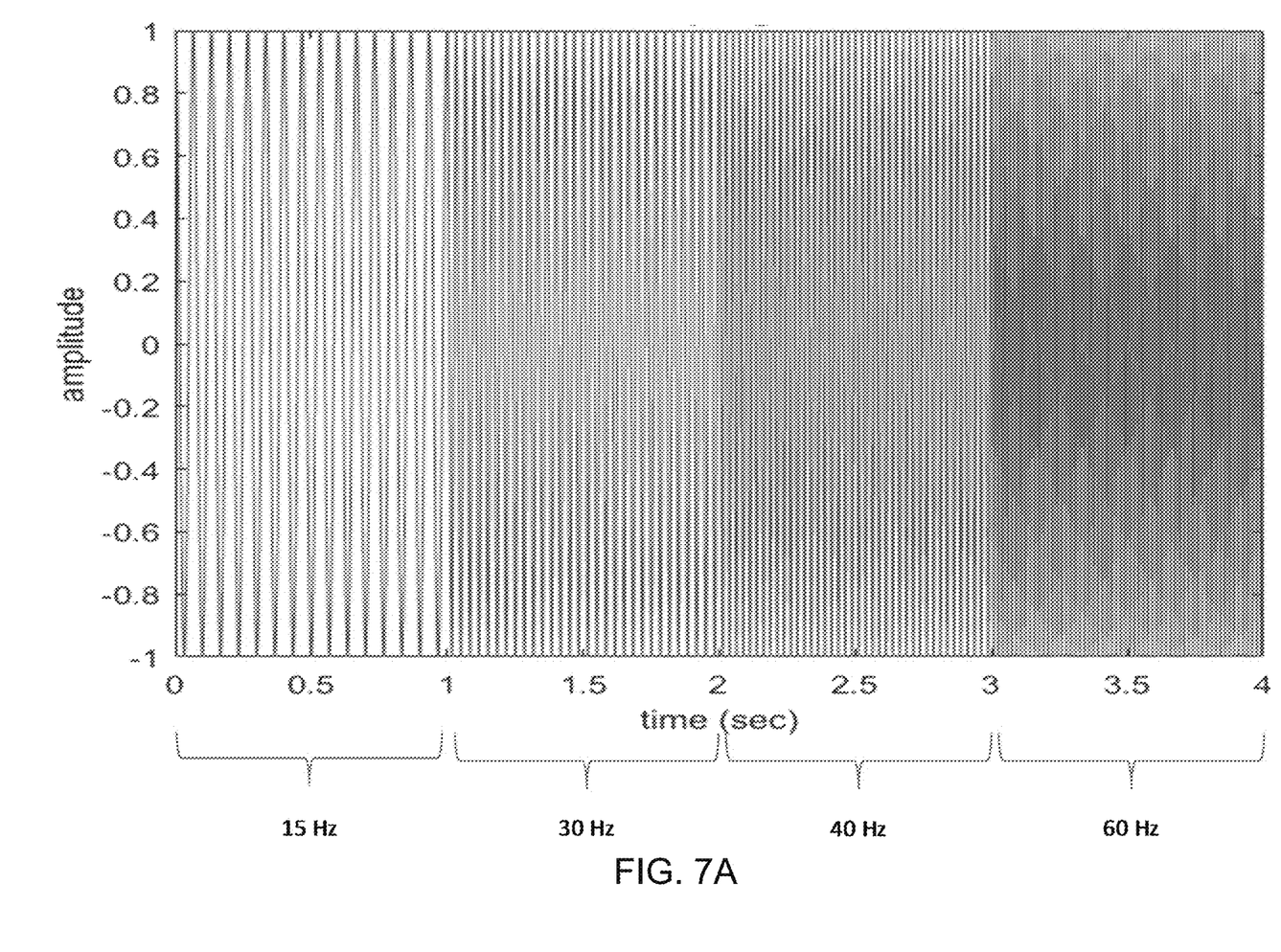
FIG. 7A shows a time plot of a chirp signal.
Figure 7B:
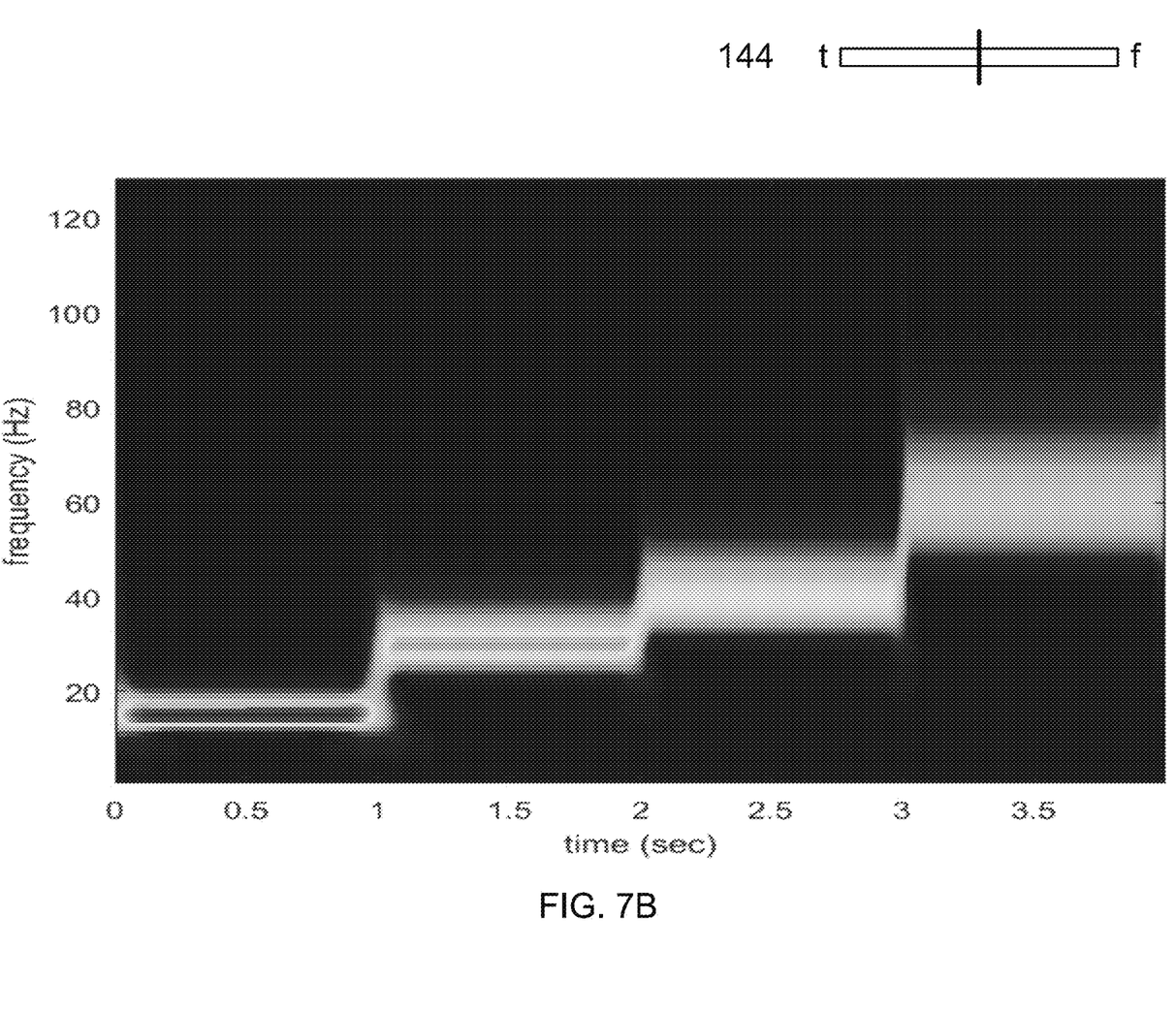
FIGS. 7B-7C show time-frequency plots of CWT analysis of MEG signals with different emphasis on time versus frequency, according to an embodiment.
Figure 7C:
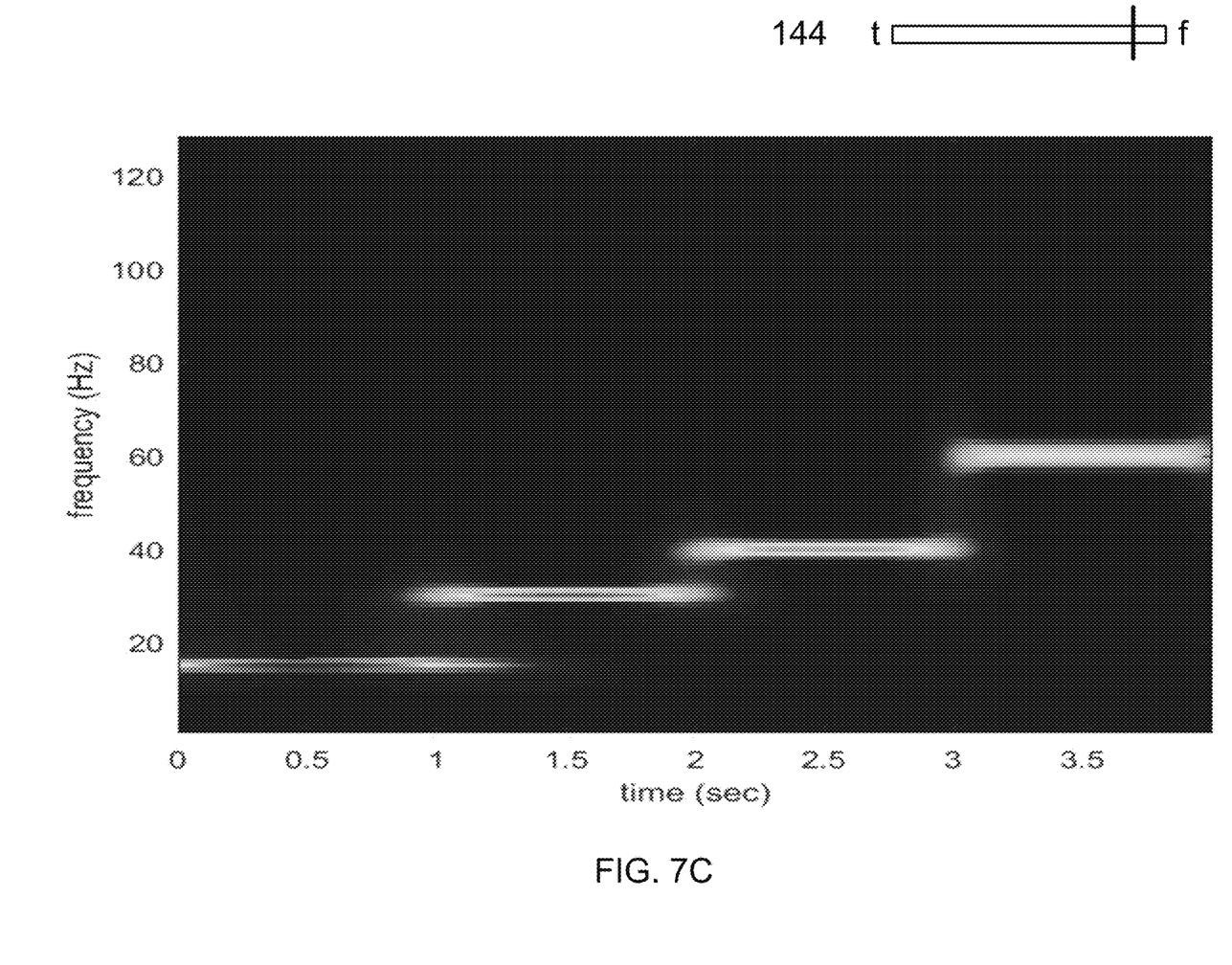

FIGS. 7A-7C give an example. FIG. 7A shows a time plot of a chirp signal. This chirp signal has four regions: 15 Hz for 0-1 sec, 30 Hz for 1-2 sec, 40 Hz for 2-3 sec and 60 Hz for 3-4 sec.

FIGS. 7B-7C show time-frequency plots of continuous wavelet transform (CWT) analysis of MEG signals with different emphasis on time versus frequency, according to an embodiment. In these figures, the color indicates the strength of the response, with warmer colors (towards red) indicating higher power. FIG. 7B is a time-frequency plot of the CWT analysis using the default center frequency of 0.75 Hz, with the decay parameter set to 3 Hz. The upper right shows a slider 144 from the user interface, where "t" indicates high time accuracy and "f" indicates high frequency accuracy. In FIG. 7B, the slider is set midway between t and f for the default parameter set.

In FIG. 7C, the user has moved the slider 144 towards the "f", indicating a desire for higher frequency accuracy. The knowledge assistant 124 increases the center frequency and adjusts the decay parameter accordingly. The resulting display in FIG. 7C has a better frequency uncertainty but with a higher time uncertainty.

Figure 8:
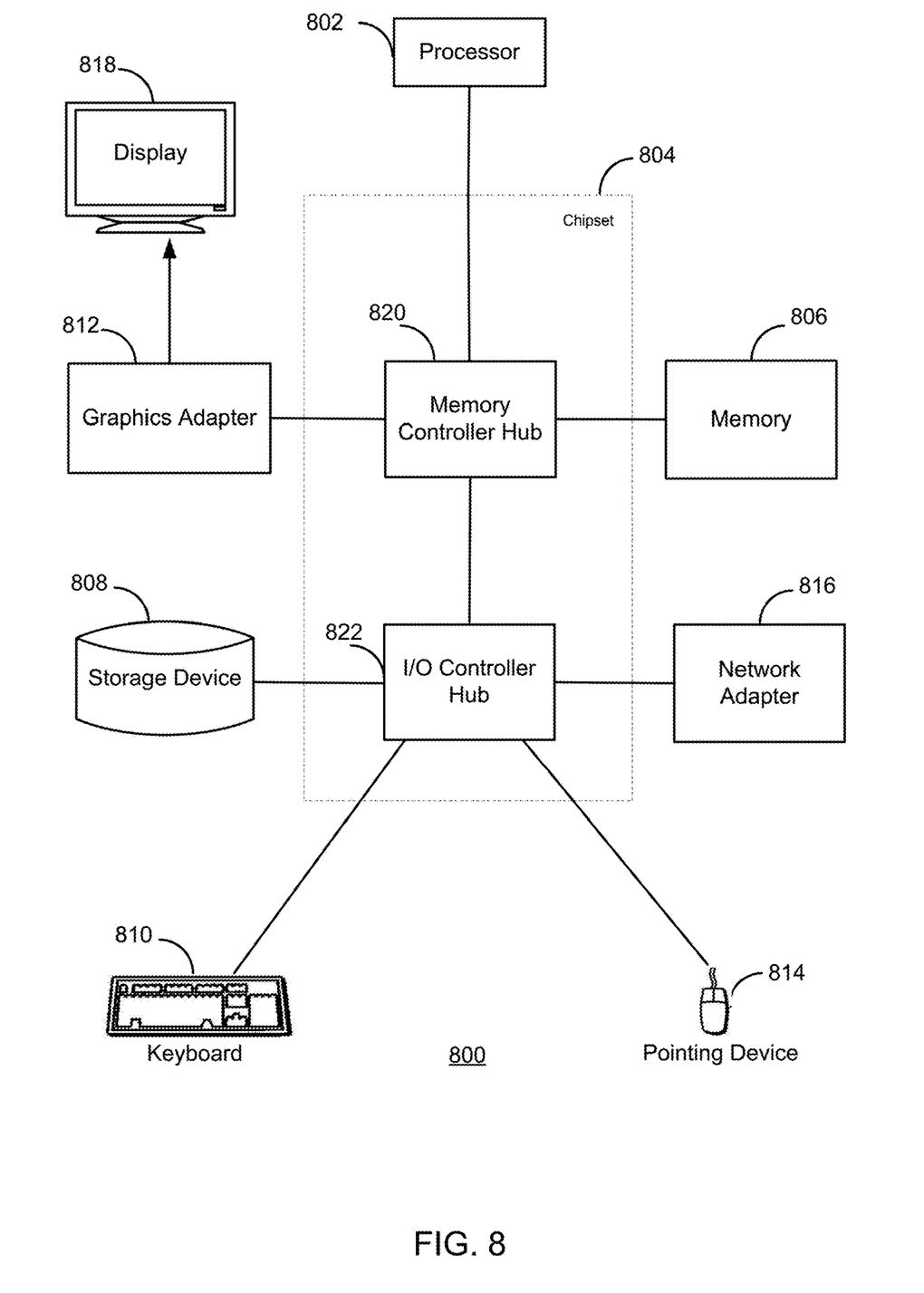
FIG. 8 shows a block diagram of a computer system, according to one embodiment.

FIG. 8 shows a block diagram of a computer system, according to one embodiment. The computer system 800 is suitable for implementing systems described above. Illustrated are at least one processor 802 coupled to a chipset 804. The chipset 804 includes a memory controller hub 820 and an input/output (I/O) controller hub 822. A memory 806 and a graphics adapter 812 are coupled to the memory controller hub 820, and a display device 818 is coupled to the graphics adapter 812. A storage device 808, keyboard 810, pointing device 814, and network adapter 816 are coupled to the U/I controller hub 822. Other embodiments of the computer 800 have different architectures. For example, the memory 806 is directly coupled to the processor 802 in some embodiments.

The storage device 808 includes one or more non-transitory computer-readable storage media such as a hard drive, compact disk read-only memory (CD-ROM), DVD, or a solid-state memory device. The memory 806 holds instructions and data used by the processor 802. The pointing device 814 is used in combination with the keyboard 810 to input data into the computer system 800. The graphics adapter 812 displays images and other information on the display device 818. In some embodiments, the display device 818 includes a touch screen capability for receiving user input and selections. The network adapter 816 couples the computer system 800 to a network. Some embodiments of the computer 800 have different and/or other components than those shown in FIG. 8.

The computer 800 is adapted to execute computer program modules for providing functionality described herein. As used herein, the term "module" refers to computer program instructions and/or other logic used to provide the specified functionality. Thus, a module can be implemented in hardware, firmware, and/or software. In one embodiment, program modules formed of executable computer program instructions are stored on the storage device 808, loaded into the memory 806, and executed by the processor 802. These may be part of a system that analyzes MEG signals post-capture, or they may be part of an (embedded) system that operates in real-time.

The approaches described above can have many advantages. For example, it can reduce the overall analysis time for doctors or other users. It also provides a way to more quickly visualize which direction the deeper analysis should be focussed on, for example whether the granularity should be increased for time or for frequency to obtain better information. By providing richer information and more intuitive manipulation of the MEG signals, it is easier for the user to identify and concentrate on the important information in the underlying signal. The above approaches also allow the user to take advantage of sophisticated signal processing techniques (such as STFT and CWT), but without requiring an understanding of the mathematics behind the tools. Instead, the user can focus on diagnosis and treatment. Automation using analytics and highlighting statistically significant data also helps in this regard, allowing the analysis to be conducted by a less experienced user.

Although the detailed description contains many specifics, these should not be construed as limiting the scope of the invention but merely as illustrating different examples. It should be appreciated that the scope of the disclosure includes other embodiments not discussed in detail above. For example, although the MEG signals were used in the examples above, the principles illustrated may be applied to other types of encephalography signals, including electroencephalography (EEG) signals. Various other modifications, changes and variations which will be apparent to those skilled in the art may be made in the arrangement, operation and details of the method and apparatus disclosed herein without departing from the spirit and scope as defined in the appended claims. Therefore, the scope of the invention should be determined by the appended claims and their legal equivalents.

What is claimed is:

1. A system for displaying magnetoencephalography (MEG) signals, the system comprising:
    an interface module that receives an MEG signal;
    an analysis module that performs a time and frequency analysis of the MEG signal, the time and frequency analysis parameterized by a parameter set that affects a tradeoff between time resolution and frequency resolution of the analysis;
    a configuration module that automatically determines values for the parameter set based at least in part on the MEG signal; and
    a user interface that displays the time and frequency analysis of the MEG signal performed using the automatically determined values for the parameter set,
    wherein:
        the user interface also receives user input defining the tradeoff between the time resolution and the frequency resolution of the analysis, the user input not expressly specifying values for the parameter set; and
        the configuration module automatically determines the values for the parameter set also based on the user input defining the tradeoff.

2. The system of claim 1 wherein the configuration module performs a Fourier transform of the MEG signal and automatically determines values for the parameter set based on frequency content of the Fourier transform.

3. The system of claim 1 wherein:
    the user input defining the tradeoff between the time resolution and the frequency resolution of the analysis specifies a relative importance between time accuracy and frequency accuracy.

4. The system of claim 1 wherein the configuration module also determines a knowledge level of the user and determines the values for the parameter set differently depending on the knowledge level of the user.

5. The system of claim 4 wherein, if the configuration module determines that the user has sufficient knowledge, the user interface allows the user to directly select the values for the parameter set.

6. The system of claim 4 wherein, if the configuration module determines that the user does not have sufficient knowledge, the user interface allows the user to specify the tradeoff between the time resolution and the frequency resolution of the analysis without expressly specifying the values for the parameter set.

7. The system of claim 1 wherein:
    the user interface receives another user input specifying a frequency band of interest; and
    the configuration module determines a range of values for another parameter set of another time and frequency analysis based on the frequency band of interest.

8. The system of claim 1 wherein:
the time and frequency analysis is a short time Fourier transform (STFT) analysis, and the parameter set for the STFT analysis includes a window size and an overlap size;
and
the configuration module automatically determines values for the window size and the overlap size based on the user input.

9. The system of claim 8 wherein the configuration module increases the window size in response to the user input increasing a relative importance of frequency accuracy.

10. The system of claim 8 wherein the configuration module determines a range of possible window sizes based on a frequency analysis of the MEG signal, and determines the value for the window size within the range based on the user input.

11. The system of claim 10 wherein the range of possible window sizes has a maximum based on a temporal size of the MEG signal.

12. The system of claim 10 wherein the range of possible window sizes has a minimum based on a primary frequency component of the MEG signal.

13. The system of claim 10 wherein the configuration module further determines the value of the overlap size as a function of the value of the window size.

14. The system of claim 1 wherein:
the time and frequency analysis is a continuous wavelet transform (CWT) analysis, and the parameter set for the CWT analysis includes a center frequency and a decay parameter;
and
the configuration module automatically determines values for the center frequency and the decay parameter based on the user input.

15. The system of claim 14 wherein the configuration module increases the center frequency in response to the user input increasing a relative importance of frequency accuracy.

16. The system of claim 14 wherein the configuration module determines a range of possible center frequencies based on a frequency analysis of the MEG signal, and determines the value for the center frequency within the range based on the user input.

17. The system of claim 14 wherein the configuration module further determines the value of the decay parameter as a function of the value of the center frequency.

18. A method implemented on a computer system comprising a processor, the processor executing instructions to effect a method for displaying magnetoencephalography (MEG) signals, the method comprising:
receiving a MEG signal;
receiving a user input defining a tradeoff between time resolution and frequency resolution of a time and frequency analysis of the MEG signal, the user input not expressly specifying values for a parameter set that affects the tradeoff between the time resolution and the frequency resolution of the analysis;
determining values for the parameter set that affects the tradeoff between the time resolution and the frequency resolution of the time and frequency analysis of the MEG signal, wherein the values are determined based on the MEG signal to be displayed and the user input defining the tradeoff;
performing the time and frequency analysis of the MEG signal using the automatically determined values of the parameter set; and
displaying the time and frequency analysis of the MEG signal performed using the automatically determined values of the parameter set.

19. A non-transitory computer-readable storage medium storing executable computer program instructions for displaying magnetoencephalography (MEG) signals, the instructions executable by a computer system and causing the computer system to perform a method comprising:
receiving a MEG signal;
receiving a user input defining a tradeoff between time resolution and frequency resolution of a time and frequency analysis of the MEG signal, the user input not expressly specifying values for a parameter set that affects the tradeoff between the time resolution and the frequency resolution of the analysis;
determining values for the parameter set that affects the tradeoff between the time resolution and the frequency resolution of the time and frequency analysis of the MEG signal, wherein the values are determined based on the MEG signal to be displayed and the user input defining the tradeoff;
performing the time and frequency analysis of the MEG signal using the automatically determined values of the parameter set; and
displaying the time and frequency analysis of the MEG signal performed using the automatically determined values of the parameter set.

\* \* \* \* \*